United States Patent [19]

Gordon et al.

[11] 4,409,203

[45] Oct. 11, 1983

[54] NON-NITROCELLULOSE NON-FORMALDEHYDE OR FORMALDEHYDE RESIN NAIL POLISH EMPLOYING AN ACRYLATE RESIN AS THE FILM FORMER

[75] Inventors: Harry W. Gordon; Nanette R. Avila, both of New York, N.Y.

[73] Assignee: Del Laboratories, Inc., Farmingdale, N.Y.

[21] Appl. No.: 377,620

[22] Filed: May 13, 1982

Related U.S. Application Data

[63] Continuation-in-part of Ser. No. 132,504, Mar. 21, 1980, abandoned.

[51] Int. Cl.$^3$ ................................................ A61K 7/04
[52] U.S. Cl. ...................................... 424/61; 424/45; 424/47; 424/49; 424/59; 424/68; 424/81
[58] Field of Search .......................................... 424/61

[56] References Cited

U.S. PATENT DOCUMENTS

| | | | |
|---|---|---|---|
| 2,173,755 | 9/1939 | Fuller | 424/61 |
| 3,277,900 | 10/1966 | Lappe | 424/61 X |
| 3,478,756 | 11/1969 | Sautter et al. | 424/61 X |
| 3,483,289 | 12/1969 | Michaelson et al. | 424/61 |
| 3,927,203 | 12/1975 | Seymour et al. | 424/61 |
| 4,058,442 | 11/1977 | Lee et al. | 424/61 |
| 4,097,589 | 6/1978 | Shansky | 424/358 |
| 4,158,053 | 6/1979 | Greene et al. | 424/78 X |
| 4,179,304 | 12/1979 | Rossomondo | 106/177 |

OTHER PUBLICATIONS

A Formulary of Cosmetic Preparations, 1977, pp. 416 and 417.

*Primary Examiner*—Dale R. Ore
*Attorney, Agent, or Firm*—Kirschstein, Kirschstein, Ottinger & Cobrin

[57] ABSTRACT

A nail polish that does not contain as a film-forming ingredient a potentially explosive nitrocellulose film former, and furthermore it does not contain formaldehyde or formaldehyde resin as a hardener which embrittles and dries the nails, and is non-allergenic and non-yellowing.

The new nail polish contains ethyl methacrylate homopolymer of a molecular weight of approximately 25,000 as the film-forming ingredient, and includes as necessary modifiers cellulose acetate propionate of a viscosity of approximately 20 seconds (ASTM method D-1343), acetyl tributyl citrate, a mixture of sucrose esters and, optionally, camphor. In addition, the new nail polish contains organic volatile solvents and is essentially water free. It also may contain other additives commonly employed in nail polishes such as polyamide resins, thickeners, pearlescents, pigments, U.V. absorbers and fragrances.

7 Claims, No Drawings

NON-NITROCELLULOSE NON-FORMALDEHYDE OR FORMALDEHYDE RESIN NAIL POLISH EMPLOYING AN ACRYLATE RESIN AS THE FILM FORMER

CROSS-REFERENCE TO RELATED APPLICATION

This application is a continuation-in-part of copending application Ser. No. 132,504, filed Mar. 21, 1980, now abandoned, for Non-Nitrocellulose Non-Formaldehyde Or Formaldehyde Resin Nail Polish Employing An Acrylate Resin As The Film Former.

BACKGROUND OF THE INVENTION

1. Field of the Invention

A nail polish in which the conventional film former, nitrocellulose, and the conventional hardener, formaldehyde or a formaldehyde resin, are omitted and, in lieu thereof, ethyl methacrylate polymer of a low molecular weight is employed as the film former.

2. Description of the Prior Art

It has been conventional for many decades to commercially use nitrocellulose as the film former for nail polish. Many other film formers have been proposed but none has come into widespread commercial use. Nitrocellulose as a film former in nail polish has various drawbacks which have been overlooked because of the low cost of nitrocellulose. Nail polishes employing this film former have been generally accepted by the public. Such polishes have many desirable attributes such as a reasonably long life, a high gloss, and an acceptable moisture vapor transmission rate. However, unmodified nitrocellulose nail polishes tend to lift off the nail and are subject to yellowing with age in the bottle.

Furthermore, nitrocellulose is basically an explosive, namely, gun cotton, so that its manufacture and transfer prior to incorporation in the nail polish represents a hazard. There are many states in the United States which do not permit the manufacture of nitrocellulose. It would be quite advantageous to provide a nail polish that does not require nitrocellulose, thereby to limit the problems created by this potential explosive.

The incorporation of formaldehyde or formaldehyde resin in a nitrocellulose nail polish also is frowned upon because they dry the nails and make the nails brittle.

Furthermore, nitrocellulose nail polishes create allergenic problems for some of their users, and nitrocellulose tends to yellow in the bottle because of its chemical instability.

It has been proposed to use other film formers in addition to or in replacement of the nitrocellulose, but none of these suggested modifications has found its way into widespread public acceptance.

By way of example, reference is made to U.S. Pat. No. 2,173,755 which suggests the substitution of non-flammable esters of cellulose for nitrocellulose, mentioning cellulose aceto butyrate and ethyl cellulose.

U.S. Pat. No. 3,483,289 mentions the addition to nitrocellulose nail polishes of material such as cellulose acetate, methyl and ethyl cellulose, benzyl cellulose, cellulose aceto propionate, cellulose aceto butyrate, alkyds, urea formaldehyde resins, melamine, casein, zein, phenol-formaldehyde and phenol-furfural resins, vinyl-polyvinyl acetate, polyvinyl chloride, polyvinyl butyrate, vinylidine chloride, copolymers of vinyl and polyvinyl acetates and butyrates, polymethyl methacrylate, polyethylacrylate, sulfonamide-formaldehyde, maleic and maleic anhydride, and linseed oil type resins.

U.S. Pat. No. 3,927,203 discloses nail polishes containing a copolymer of at least one alkoxy alkyl acrylate or methacrylate with at least one different alkoxy alkyl acrylate or methacrylate or at least one hydroxy alkyl acrylate or methacrylate and, optionally, a minor amount of a further monomer.

U.S. Pat. No. 4,097,589 discloses a nail polish whose basic film former is nitrocellulose but which also includes a copolyamide.

U.S. Pat. No. 4,126,675 discloses a nail polish whose basic film former is nitrocellulose but which also may include acrylate copolymers of methyl methacrylate and hexyl methacrylate.

U.S. Pat. No. 4,158,053 discloses a nail polish of the water-base type in which the film former is an aqueous emulsion polymer of acrylates and methacrylates and, optionally, styrenes.

U.S. Pat. No. 4,179,304 discloses a nail polish containing nitrocellulose as the film former, formaldehyde resin as the hardener, and a mixture of sucrose esters as modifiers. Other film forming resins whose use is mentioned are cellulose propionate, cellulose acetate butyrate, ethyl cellulose, and acrylic resins which are homopolymers and copolymers of alkyl acrylates and methacrylates.

Finally, Australian Pat. No. 64,458 of 1965 discloses a nail polish which employs as the film former one or a combination of resins selected from the group consisting of polyvinyl alcohol, polyvinyl acetate, polyamide resins, acrylic resins, cyclic ketones, nitrocellulose, ethyl cellulose, methyl cellulose, and modified resin derivatives, all characterized by their solubility in alcohol, water, or low odor aliphatic or aromatic hydrocarbon solvents or blends thereof.

SUMMARY OF THE INVENTION

1. Purposes of the Invention

It is the primary object of this invention to provide a nail polish which is free of nitrocellulose and free of formaldehyde and formaldehyde resins, and which essentially consists of ethyl methacrylate having a molecular weight of approximately 25,000 as the film-forming ingredient, including as necessary modifiers certain additives which improve the physical characteristics of the nail polish film and, as optional additives, further modifiers such as are conventionally employed in nail polishes.

It is another object of the invention to provide a nail polish of the character described in which the necessary modifiers include cellulose acetate propionate of a viscosity of approximately 20 seconds (ASTM method D-1343), acetyl tributyl citrate and a mixture of sucrose esters, with camphor as an optional modifier.

It is another object of the invention to provide a nail polish of the character described in which the conventional modifiers that may be included in the formulation are ingredients such as polyamide resins, thickeners, pearlescents, pigments, U.V. absorbers and fragrances.

It is another object of the invention to provide a nail polish of the character described which, despite the substitution of a new chemical ingredient for the film former in place of nitrocellulose and despite the provision of hardening ingredients other than formaldehyde and formaldehyde resins, has a life as long as that of a conventional nitrocellulose nail polish, dries as quickly, applies as easily, has as good a gloss, is just as hard, adheres as well to the nail, is as easily removed by solvents, is as flexible, has a comparable viscosity, and has a vapor moisture transmission that is at least as good.

It is another object of the invention to provide a nail polish of the character described employing a film former which is less dangerous to manufacture and yet is not unduly expensive.

It is another object of the invention to provide a nail polish of the character described which can be formulated to provide a clear film or can be modified to provide a colored transparent or a colored opaque film or a pearlescent film, as desired.

It is another object of the invention to provide a nail polish of the character described which is essentially nonallergenic, does not tend to unduly harden or crack the nails, and which does not yellow the nails.

Other objects of the invention in part will be obvious and in part will be pointed out hereinafter.

2. Brief Description of the Invention

The new nail polish is a viscous liquid with a high solids content dissolved in an organic volatile solvent which will dry sufficiently rapidly for practical use to leave a hard, glossy, detergent-resistant film that is smooth and has an excellent sheen, and is uninterrupted by cracks or crazing. For the film former there is employed an ethyl methacrylate homopolymer made by the Commercial Resins Division of Dupont Plastic Products and Resins Department under the trademark Elvacite 2043, this being a plastic of low molecular weight in the order of 25,000. The physical fingerprints of this resin are furnished at a later portion of the present specification. The amount of ethyl methacrylate polymer ranges from 10% to 25% by weight of the nail polish.

For necessary modifiers there are employed cellulose acetate propionate of a viscosity of approximately 20 seconds (ASTM method D-1343), acetyl tributyl citrate, and a mixture of sucrose esters sold by cellofilm Corp. of Wood-Ridge, New Jersey under the trademark CV-170. An optional modifier is camphor. The cellulose acetate propionate is present in an amount of about 0.5% to about 6% by weight of the nail polish, the acetyl tributyl citrate is present in an amount of from about 2% to 6% by weight of the nail polish, and the mixture of sucrose esters is present in an amount of from about 2% to about 6% by weight of the nail polish. The camphor varies from about 0% to about 3% by weight of the nail polish.

A mixture of solvents is employed which are organic and volatile and are essentially anhydrous. Typical solvents are isopropyl alcohol (95%+, essentially anhydrous), ethyl acetate, butyl acetate and methyl ethyl ketone; these total approximately 70% by weight of the nail polish. Other suitable solvents are acetone, amyl acetate, methyl acetate, ethanol (95%+, essentially anhydrous), Cellosolve, toluene, xylene and mixtures thereof.

There are no acceptable substitutes for the cellulose acetate propionate of the specified viscosity, nor for the acetyl tributyl citrate, nor for the mixture of sucrose esters.

There also may be present in the nail polish the conventional modifiers to adapt the nail polish to any particular marketing requirements. These include polyamide resins, thickeners, pearlescents, pigments, dyes, U.V. absorbers and fragrances.

DESCRIPTION OF THE PREFERRED EMBODIMENTS

Set forth below are the active ingredients which have been referred to above, together with their maximum range by weight in the nail polish and their ideal range by weight.

| Active Ingredients | Maximum Range by Weight | Ideal Range by Weight |
|---|---|---|
| Ethyl, methyl, butyl, or isobutyl methacrylate homopolymers | 10-25% | 13-16% |
| Cellulose acetate propionate (viscosity approximately 20 seconds) [ASTM method D-1343] | 0.5-6.0% | 3-5% |
| Acetyl tributyl citrate | 2-6% | 4-5% |
| Mixture of sucrose esters (CV-170) | 2-6% | 4-5% |
| Camphor | 0-3% | 0-2% |
| Ethyl methacrylate methylacrylate copolymer (for use as a luster enhancing agent) | 0-15% | 5-10% |

The methacrylate homopolymers are fast-dissolving, low-viscosity resins with alcohol solubility. They have excellent pigment-wetting ability and have a broad solubility. Their molecular weights are approximately 25,000. Their density in kilograms of the resin per cubic meter is 1140 (in lbs. per gallon 9.51). They have a bulking value of 0.1051 gallons per lb. The test employed for density and bulking value is ASTM D-1475, the density calculation being that of 20% solutions of the resin in methyl ethyl ketone. Their specific gravity at 25°/25° C. is 1.14 calculated from a water density equal to 997 kilograms per cubic meter. Their glass transition temperature is 65° measured by differential thermal analysis as described in ASTM D-3418. Their Tukon hardness has a value of Knoop #11 measured at 23° C. and 50% RH on the Tukon tester at 25-g load using a 1.6 mm. thick disc prepared by compression molding the polymer in bead form. It is noted that this hardness reading on the molded specimen reflects inherent hardness with the resin without the reinforcing effect of a rigid substrate. Such readings are consistently lower than corresponding hardness readings for thin coatings on glass or metal substrates. They have an acid number of 8 measured as milligrams of potassium hydroxide per gram of polymer. Their tensile strength at 23° C., 50%RH, has an MPa value of 7 and a psi of 1000, being determined with the use of compression molded samples. Their elongation at break using a sample at 23° C., 50% RH, has a percentage value of less than 1. Their typical viscosity in toluene, mPa.s (cP) at 25° is 300. Their percentage of solids as furnished by Dupont is 37.5. They are insoluble in methyl alcohol, cyclohexanol, ethylene glycol, glycerol, formamide, diisopropyl ether, trichlorotrifluoroethane, n-hexane, cyclohexane, VM & P naphtha, mineral spirits, turpentine, castor oil, and alkali refined linseed oil. They are soluble in ethyl alcohol, n-propyl alcohol, isoamyl alcohol, dimethyl formamide, methylene chloride, ethylene dichloride, perchlorethylene, methyl formate, isopropyl acetate, butyl lactate, ethylene glycol monoethyl ether acetate, diethyl ether, tetrahydrofuran, methyl isobutyl ketone, diisobutyl ketone, cyclohexanone, isophorone, "Pentoxone" solvent, diacetone alcohol and acetonitrile, as well as the solvents mentioned previously in connection with the formulation of the nail polish. They form a cloudy solution with trichlorofluoromethane, "Freon" TMC solvent which is an azeotrope of trichlorotrifluoroethane and methylene chloride, nitromethane and nitroethane.

The cellulose acetate propionate employed is one having a viscosity of about 20 seconds as determined by ASTM method D-1343 in the solution described as Formula A ASTM method D-817. It is made by Eastman Chemical Products, Inc. and has the following physical fingerprints:

| | |
|---|---|
| Acetyl content in weight percentage on the average | 2.5 |
| Propionyl content in weight percentage on the average | 46.3 |
| Hydroxyl content in weight percentage on the average | 2.07 |
| Color in particles per million; haze is 50, both color and haze determinations being made on the same solution used for viscosity determination using Pt-Co color standards and Johns-Manville Celite (diatomaceous silica products) haze standards | 300 |
| Melting point range | 200–210° C. |
| Free acidity as acetic acid, weight percentage | 0.02 |
| Ash, weight percentage | 0.017 |
| Refractive index, $n_D^{25°\ C.}$ | 1.475 |
| Specific gravity, 25° C./25° C. | 1.23 |
| Weight/volume, 20° C. lb./U.S. gal. | 10.2 |

The product is sold by Eastman Chemical Products under the trademark CAP-482-20.

The acetyl tributyl citrate employed is sold by the Special Chemicals Department of Pfizer, Inc. under the trademark Citroflex A-4 and has the following physical fingerprints:

| | |
|---|---|
| Boiling point at 1 mm. of mercury | 173° C. |
| Vapor pressure at 1 mm. of mercury at 170° C. | 0.8 |
| Vapor density compared to air | 14.1 |
| It is insoluble in water. | |
| Specific gravity at 25° C. | 1.045–1.055 |

Its toxicology is documented in the magazine "Toxicology and Applied Pharmacology", Vol. 1, No. 3, May 1959, pp. 283–298

| | |
|---|---|
| Molecular weight | 402.5 |
| Refractive index, 25° C. | 1.441 |
| Weight per gallon, 25° C. | 8.74 lb. |
| Pour point | −75° F. |
| Viscosity, 25° C. | 42.6 cps. |
| Flash point (Cleveland open cup) | 204° C. |
| Free acidity (as citric acid) after 1 hr., 150° C. | 0.10% max. |
| Assay, minimum | 99.0% |
| Acidity (as citric acid), maximum | 0.02% |
| Color, maximum | 50 APHA |
| Water (Karl Fischer), maximum | 0.25% |
| Odor | Odorless |

The mixture of sucrose esters is sold by Cellofilm Corporation under the trademark CV-170, which is a composition including sucrose benzoate, sucrose acetate isobutyrate, toluene or butyl acetate, dibutyl phthalate, and methyl methacrylate copolymer. CV-170 is embraced by the additives to the nitrocellulose formulation disclosed in U.S. Pat. No. 4,179,304.

Conventional camphor is employed, this being a ketone derived from the wood of the camphor tree in its natural form, *Cinnamomum camphora*, a synthetic camphor having the formula

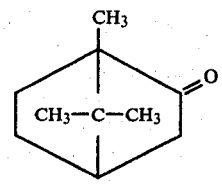

It is also known as 2-bornanone and gum camphor.

It is preferred also to employ a luster enhancing agent for which the desired formulation utilizes Acryloid B-72 made by ROHM and HAAS COMPANY of Philadelphia, Pa., which constitutes a copolymer of 75% ethyl methacrylate and 25% methacrylate.

The solvents mentioned above are conventional and need not be detailed.

Typical thixotropic agents which could be used are diatomaceous earths, colloidal silica, and quaternerized Montmorillonite clays such as stearylkonium hectorite.

Typical pearlescents are guanine (natural pearl), bismuth oxychloride and titanium dioxide-coated mica.

For a pigment or dye, conventional materials can be employed. Suitable ones are listed in "The Chemistry and Manufacture of Cosmetics" by Madison G. DeNavarre, Vol. 2, Second Edition, pp. 996–998.

Ultra-violet absorbers typically are utilized to inhibit the action of U.V. radiation from deteriorating the various chemicals employed for the film and to prevent fading of the pigment or dye. Those which may be usefully employed in the instant nail polish formulation are listed in Encyclopedia of Chemical Technology under the heading "U.V. Absorbers", Vol. 21, 1969, pp. 115–122.

Any suitable fragrances can be added.

An example of a typical formulation embodying the present invention is as follows:

EXAMPLE

| Ingredients | % W/W |
|---|---|
| Isopropyl alcohol (95%+, essentially anhydrous) | 5.90 |
| Ethyl acetate | 9.90 |
| Butyl acetate | 31.60 |
| Methyl ethyl ketone | 25.00 |
| CV-170 | 3.8 |
| Citroflex A-4 (acetyl tributyl citrate) | 2.94 |
| Camphor | 1.05 |
| Elvacite 2043 (ethyl methacrylate homopolymer) | 10.36 |
| CAP 482-20 (cellulose acetate propionate) | 3.01 |
| Acryloid B-72 | 7.0 |

The total percentage of active ingredients (aside from the organic volatile solvents) is about 30.

The aforesaid formulation is an excellent nail polish. It has an excellent ease of application when brushed on the nail. Its drying time is as follows:

| | |
|---|---|
| Sufficiently set to touch | 3 minutes |
| Tack free | 6 minutes |

| | |
|---|---|
| Dried through | 9 minutes |
| Dried hard | 20 minutes |

These times are for a single film application 3 mils thick, using as the testing procedure ASTM D-1640.

The gloss of the dried film at a 60° angle of incidence is about 100%. Its gloss at a 20° angle of incidence is about 81%. Its Sward hardness is 30 oscillations. Its adhesion to the nail using the cross-cut method is about 90%. Its Taber abrasion is 49 milligrams lost. It can be removed from the nail very easily and quickly with acetone. Its flexibility is excellent—it passed the ⅛" rod test. Its vapor moisture transmission is unusually good, being about $6 \times 10^{-3}$ grams/24 hours/cm², in this respect being better than most nitrocellulose nail polishes. Its viscosity measured on a Brookfield viscosimeter using a #2 spindle at speed 6 for 1 minute is 384 cps, and when given an accelerated life test at 40° C. for 6 weeks, it did not yellow in the bottle.

When compared with a standard high-quality prior art nail polish employing a nitrocellulose film former and a formaldehyde hardener, the new nail polish was as easy to apply and was equal in appearance. Its wear rating at the end of 24 hours and 48 hours was essentially the same. Thus, despite the fact that an entirely new formulation has been employed for the film-forming ingredients, the net result is absence of degradation in the polish as applied.

It thus will be seen that there is provided a nail polish which achieves the various objects of the invention and which is well adapted to meet the conditions of practical use.

As various possible embodiments might be made of the above invention, and as various changes might be made in the embodiments above set forth, it is to be understood that all matter herein described is to be interpreted as illustrative and not in a limiting sense.

We claim:

1. A liquid nail polish for application to human nails, said polish constituting a liquid composition consisting essentially of: from about 10% to about 25% of a methacrylate homopolymer having a molecular weight of about 25,000 as the principal film-forming constituent, selected from the group consisting of methyl methacrylate, ethyl methacrylate, butyl methacrylate and isobutyl methacrylate homopolymers, from about 0.5% to about 6.0% of cellulose acetate proprionate, from about 2% to about 6% of acetyl tributyl citrate, from about 2% to about 6% of a mixture of sucrose esters, and from about 0% to about 3% of camphor, all the foregoing percentages being based upon the weight of the liquid nail polish, said polish being free of nitrocellulose and of formaldehyde and formaldehyde resins, said polish also including an organic volatile solvent in which the homopolymer is dissolved, selected from the group consisting of isopropyl alcohol, ethyl acetate, butyl acetate, methyl ethyl ketone, acetone, amyl acetate, methyl acetate, ethanol, Cellosolve, toluene, xylene and mixtures thereof, and being essentially water free.

2. A liquid nail polish as set forth in claim 1, wherein the percentage by weight of the liquid nail polish of ethyl methacrylate homopolymer is from about 13% to about 16%, of cellulose acetate proprionate is from about 3% to about 5%, of acetyl tributyl citrate is from about 4% to about 5%, of the mixture of sucrose esters is from about 4% to about 5%, and of camphor is from about 0% to about 2%.

3. A liquid nail polish as set forth in claim 1, wherein the viscosity of the cellulose acetate proprionate is about 20 seconds by ASTM method D-1343.

4. A liquid nail polish as set forth in claim 1, wherein the mixture of sucrose esters is a composition including sucrose-benzoate, sucrose acetate isobutyrate, toluene acetate, butyl acetate, dibutyl phthalate, and methyl methacrylate copolymer.

5. A liquid nail polish as set forth in claim 1, including the following constituents:

| Ingredients | % by weight of the liquid nail polish |
|---|---|
| Essentially anhydrous isopropyl alcohol | 5.9 |
| Ethyl acetate | 9.9 |
| Butyl acetate | 31.6 |
| Methyl ethyl ketone | 23.5 |
| Mixture of sucrose esters | 4.4 |
| Acetyl tributyl citrate | 4.2 |
| Camphor | 1.5 |
| Ethyl methacrylate homopolymer | 14.8 |
| Cellulose acetate proprionate | 4.3 |

6. A liquid nail polish as set forth in claim 1, which additionally includes about 0% to 7% of a copolymer of ethyl methacrylate and methacrylate.

7. A liquid nail polish as set forth in claim 1, including the following constituents:

| Ingredients | % by weight of the liquid nail polish |
|---|---|
| Essentially anhydrous isopropyl alcohol | 5.9 |
| Ethyl acetate | 9.9 |
| Butyl acetate | 31.6 |
| Methyl ethyl ketone | 25.00 |
| CV-170 (a mixture of sucrose esters) | 3.08 |
| Citroflex A-4 (acetyl tributyl citrate) | 2.94 |
| Camphor | 1.05 |
| Elvacite 2043 (ethyl methacrylate homopolymer) | 10.36 |
| CAP 482-20 (cellulose acetate propionate) | 3.01 |
| Acryloid B-72 (a copolymer of 75% ethyl methacrylate and 25% methacrylate) | 7.0 |

* * * * *